United States Patent
Fu et al.

(10) Patent No.: US 11,348,236 B2
(45) Date of Patent: May 31, 2022

(54) AUTOMATED VISUAL INSPECTION OF SYRINGES

(71) Applicant: Landing AI, Grand Cayman (CI)

(72) Inventors: Wei Fu, Newark, CA (US); Rahul Devraj Solanki, Sunnyvale, CA (US); Mark William Sabini, Palo Alto, CA (US); Yuanzhe Dong, Palo Alto, CA (US); Hao Sheng, Newark, CA (US); Gopi Prashanth Gopal, Redmond, WA (US); Ankur Rawat, Sunnyvale, CA (US); Sanjeev Satheesh, Mountain View, CA (US)

(73) Assignee: Landing AI, Grand Cayman (KY)

( * ) Notice: Subject to any disclaimer, the term of this patent is extended or adjusted under 35 U.S.C. 154(b) by 66 days.

(21) Appl. No.: 16/845,993

(22) Filed: Apr. 10, 2020

(65) Prior Publication Data

US 2021/0192723 A1    Jun. 24, 2021

Related U.S. Application Data

(60) Provisional application No. 62/952,199, filed on Dec. 20, 2019.

(51) Int. Cl.
| | |
|---|---|
| G06T 7/00 | (2017.01) |
| G06T 7/194 | (2017.01) |
| G06K 9/62 | (2022.01) |
| A61M 5/31 | (2006.01) |

(52) U.S. Cl.
CPC ......... *G06T 7/0012* (2013.01); *A61M 5/3129* (2013.01); *G06K 9/6227* (2013.01); *G06T 7/194* (2017.01); *A61M 2005/3132* (2013.01); *G06T 2207/10016* (2013.01); *G06T 2207/20081* (2013.01); *G06T 2207/20084* (2013.01); *G06T 2207/20224* (2013.01); *G06T 2207/30004* (2013.01); *G06T 2210/12* (2013.01)

(58) Field of Classification Search
None
See application file for complete search history.

(56) References Cited

U.S. PATENT DOCUMENTS

| | | |
|---|---|---|
| 2012/0106837 A1 | 5/2012 | Partis et al. |
| 2015/0253289 A1 | 9/2015 | Bardina et al. |
| 2016/0379376 A1 | 12/2016 | Milne et al. |
| 2017/0032192 A1 | 2/2017 | Teichman et al. |

(Continued)

OTHER PUBLICATIONS

Automated Machine Vision System for Liquid Particle Inspection of Pharmaceutical Injection, by Zhang, et al , IEEE Transactions on instrumentation and measurement, vol. 67, No. 6, Jun. 2018 (Year: 2018).*

(Continued)

*Primary Examiner* — Vikkram Bali
(74) *Attorney, Agent, or Firm* — Fenwick & West LLP (57) ABSTRACT

A processor receives an image of a syringe. After identifying a background and foreground of the image, where the foreground indicates pixels that may be associated with a defect, the processor subtracts the background to generate an updated image with an accentuated foreground. The processor applies a bounding box to a group of pixels in the foreground and inputs the bounding box into a classifier. The classifier outputs a label indicating whether the syringe is defective.

20 Claims, 5 Drawing Sheets

(56) References Cited

U.S. PATENT DOCUMENTS

2017/0056603 A1 3/2017 Cowan et al.
2019/0164275 A1 5/2019 Rusch et al.

OTHER PUBLICATIONS

Hinsch, B. "Inspection Technologies for Glass Syringes," ONdrugDelivery Magazine, Sep. 2014, pp. 35-38, No. 52.
PCT International Search Report and Written Opinion, PCT Application No. PCT/US2020/063701, dated Mar. 18, 2021, 20 pages.

* cited by examiner

AUTOMATED VISUAL INSPECTION OF SYRINGES

CROSS-REFERENCE TO RELATED APPLICATIONS

This application claims the benefit of U.S. Provisional Application No. 62/952,199, filed Dec. 20, 2019, the disclosure of which is hereby incorporated by reference in its entirety.

TECHNICAL FIELD

This disclosure generally relates to automating the visual inspection of objects, and more particularly relates to detecting defects in syringes using artificial intelligence.

BACKGROUND

After manufacture and prior to use by pharmaceutical entities, a syringe must be inspected for defects that may contaminate contents of the syringe. Conventional methods require human inspection of the syringe, a process that is expensive, error-prone, and consumes a large amount of time and manual effort. Moreover, given the unique nature of syringes, whose reason for being defective may depend on floating particles in liquid of the syringe, conventional machine learning models are ill-equipped to determine whether a syringe is defective.

SUMMARY

After manufacture, a syringe may include contaminants, such as dust or fiber particles, as well as bubbles. The system described herein uses machine learning techniques and heuristics to distinguish between contaminants and bubbles. The system receives an image of the syringe that includes a foreground and a background. The system removes the background, accentuating the foreground, and applies a bounding box to pixels that may be associated with a contaminant. The bounding box is input to a classifier, which outputs a label indicating whether the syringe is defective (e.g., includes contaminants), or not.

BRIEF DESCRIPTION OF THE DRAWINGS

The disclosed embodiments have other advantages and features which will be more readily apparent from the detailed description, the appended claims, and the accompanying figures (or drawings). A brief introduction of the figures is below.

DETAILED DESCRIPTION OF THE DRAWINGS

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

The systems and methods described herein use machine learning techniques to automate the inspection of syringes after manufacture. A camera captures an image of the syringe such that the image includes a background. A processor accentuates a portion of the image with the syringe (e.g., a foreground) and subtracts the background from the image to generate an updated image. The processor applies a bounding box to pixels in the updated image and inputs the pixels within the bounding box to a classifier. The pixels within the bounding box are associated with an object that may be a defect. The classifier outputs a label indicating whether the syringe contains a defect (e.g., a contaminant).

In some embodiments, the camera captures a number of images of the syringe over a span of time. The syringe, filled with fluid, is agitated briefly such that any objects within the syringe also may move when the syringe is in motion. When the syringe stops moving, and the objects in the syringe begin to settle, the camera captures a series of images of the syringe. In some embodiments, the processor removes the background from the image after processing the series of images of the syringe.

The images of the syringe after it has been agitated may also help mitigate false positive results from the classifier; a false positive result is one that inaccurately labels an object as a defect, which thus yields to a syringe being labeled as defective when it is not in fact defective.

Responsive to the classifier outputting a label indicating that the syringe is defective and/or that an object in the syringe is a potential defect, the processor tracks trajectories of objects within the syringe across multiple frames to determine whether the trajectory is similar to that of a defect. In some embodiments, after the classifier determines that the object is a potential defect, and the processor tracks a trajectory of the object, the processor outputs a label indicating that the syringe is defective.

The use of a machine learning classifier facilitates the automation of visually inspecting syringes after they are manufactured and applying heuristics to trajectories of objects identified within the syringes evaluates the accuracy of the machine learning classifier's output. Thus, the process described herein greatly reduces the manual effort and time required to check for defects before the syringes are sent out to pharmaceutical vendors.

Figure 1:
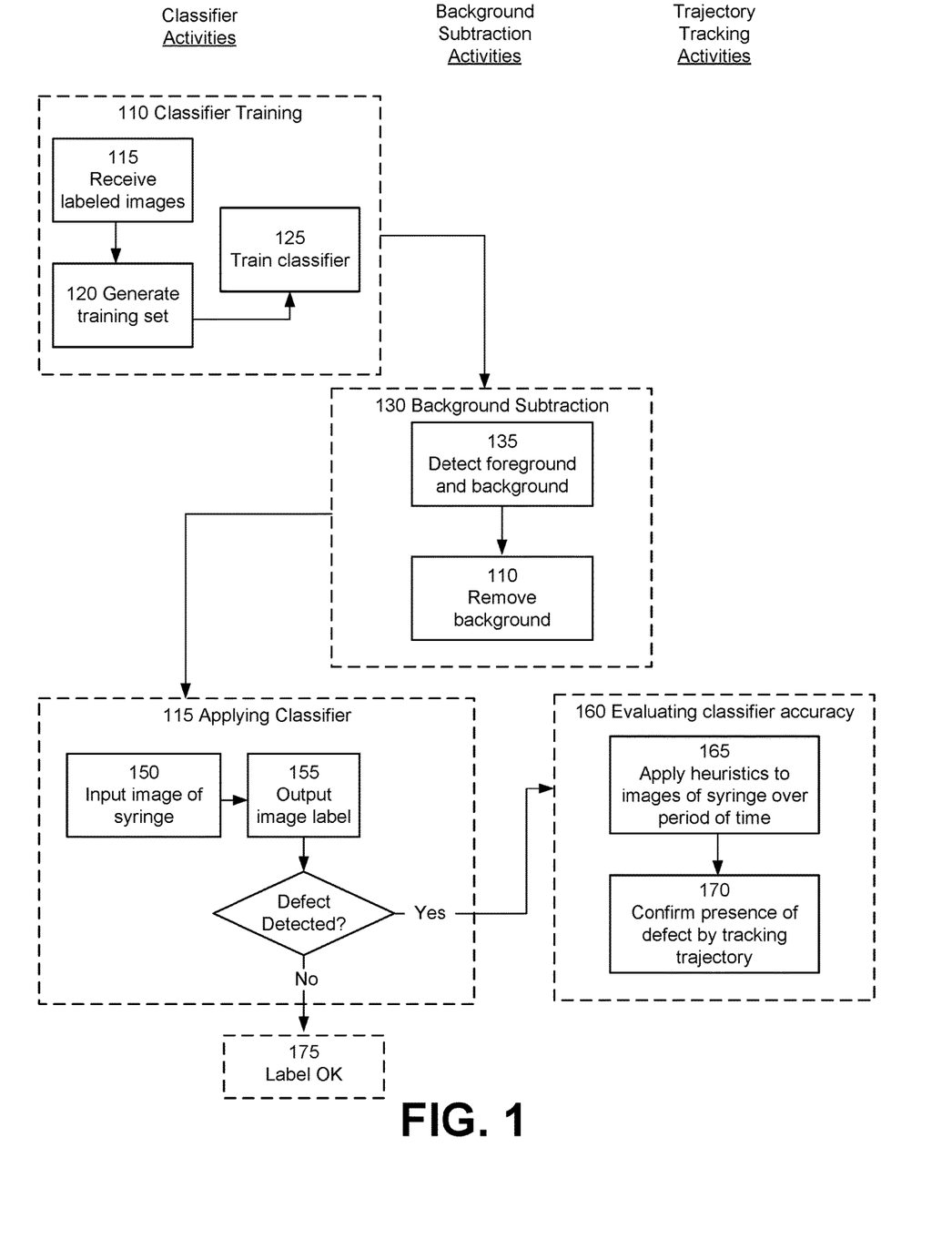
FIG. 1 is a flow diagram for training and applying a classifier that detects defects in images of syringes, in accordance with one or more embodiments.

FIG. 1 depicts a flow diagram for training and applying a classifier that detects defects in images of syringes, in accordance with one or more embodiments. A defect is an object that may contaminate contents of the syringe. Types defects include, for example, glass, dust, dirt, silastic, and fibers, among others. An air bubble in fluid within the syringe is not a defect. To detect a defect in an image of a syringe, a processor trains 110 a classifier, subtracts 130 a background from the image of the syringe to form an updated image, applies 115 the trained classifier to the updated image, and responsive to the output of the classifier indicating that the syringe is defective, evaluates 160 the accuracy of the classifier output. In some embodiments, the process of detecting defects in an image of a syringe differs from what is shown in FIG. 1.

The processor trains 110 a classifier to identify defective images of syringes. The processor receives 115 labeled images, generates 120 a training set from the labeled images, and trains 125 the classifier using the training set. The received labeled images are labeled, by humans, as either not defective or defective. Each of the images labeled as defective include at least one bounding box indicating a location of a potential defect in the image. In some embodiments, each of the received images are also labeled, by humans, with a type of defect. Images labeled as not defective may include labels of objects that are not considered defects, such as bubbles. After receiving initial training data, in some embodiments, the processor generates artificial images of defective and not defective syringes to add to the training set using conventional artificial intelligence and machine learning techniques.

Figure 2A:
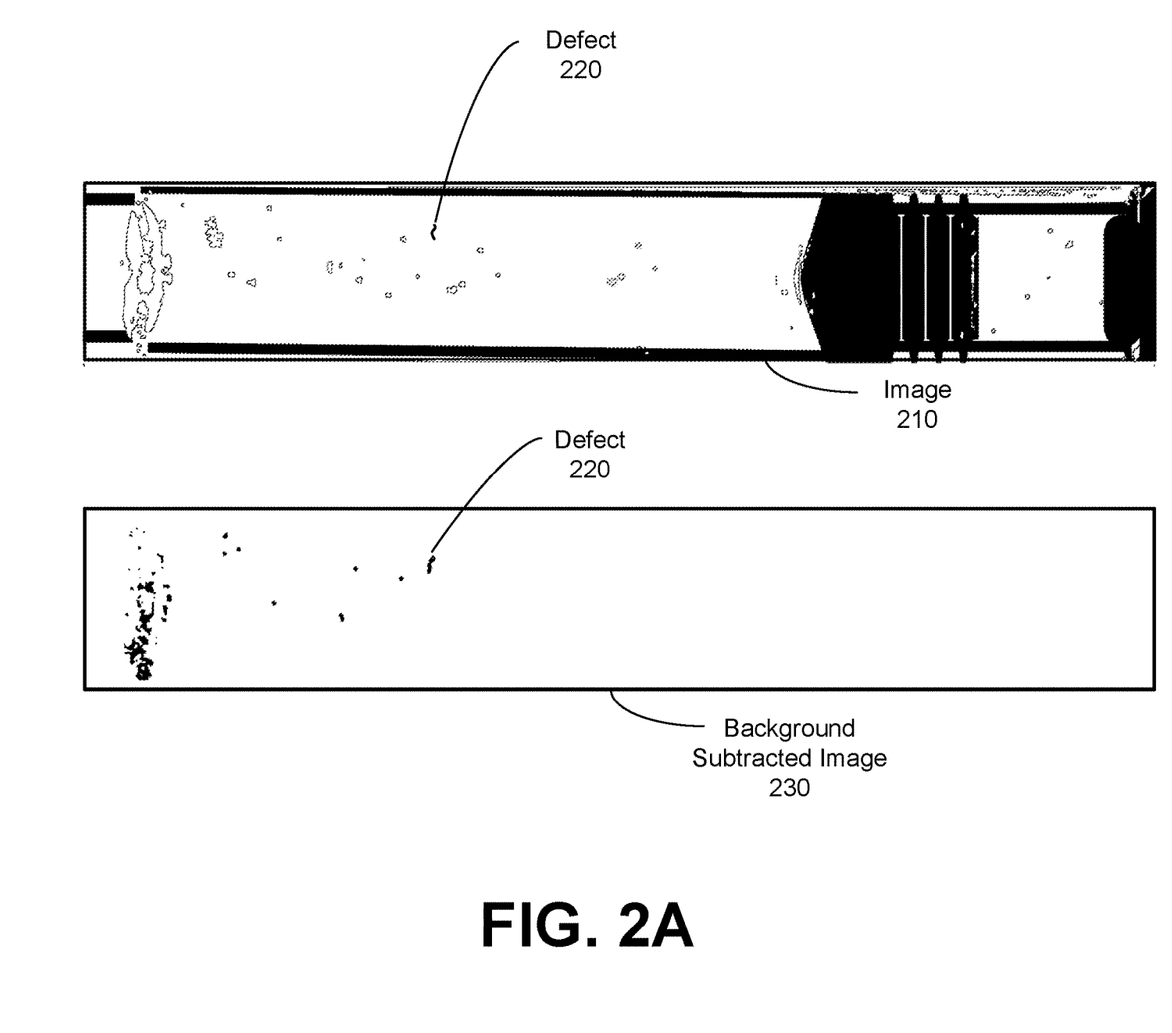
FIGS. 2A-B show example training data for training a machine learning classifier that detects defects in images of syringes, in accordance with one or more embodiments.
Figure 2B:
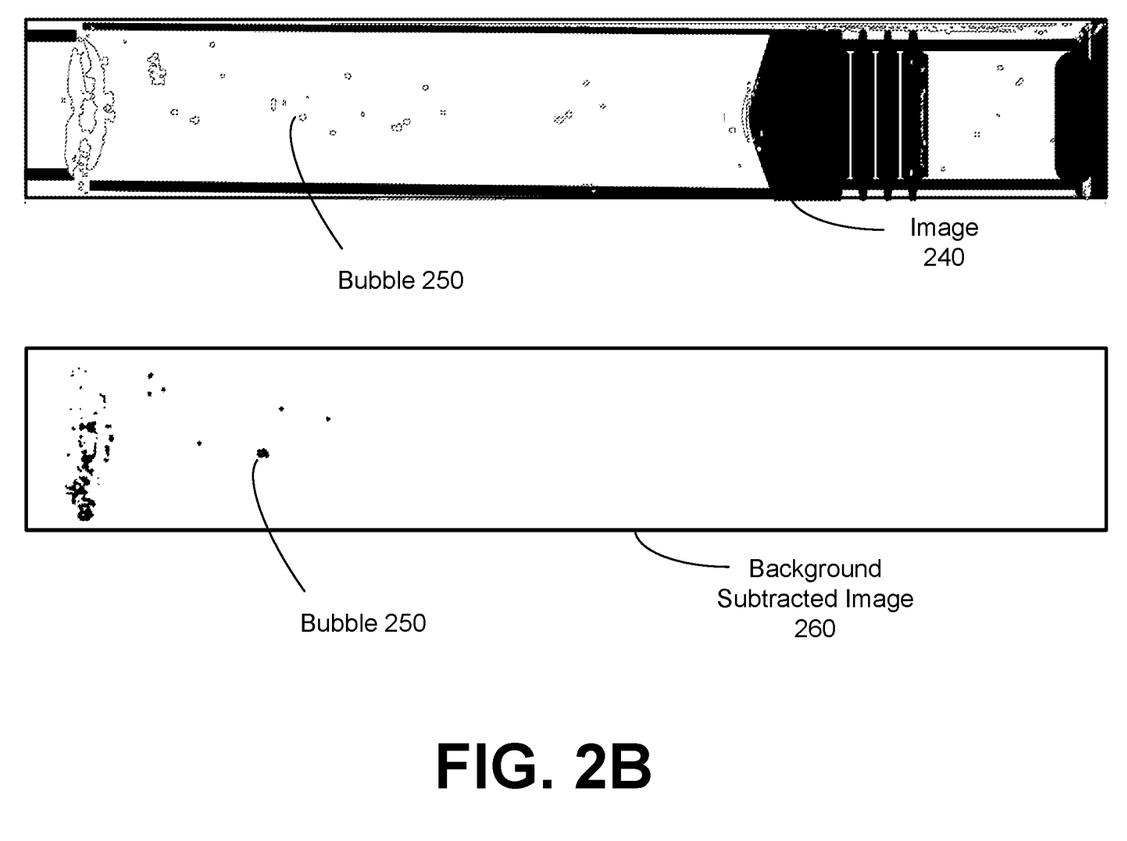

The processor generates 120 the training set from the labeled images. In some embodiments, the training set includes a positive training set and a negative training set. The positive training set includes images of defective syringes that are labeled as defective, and in some embodiments, the types of defects associated for each of the images of defective syringes. The negative training set includes images of syringes that do not include defects as well as images of syringes that include objects that are not defects (e.g., bubbles), and are therefore labeled as not defective. FIG. 2 shows in further detail the types of training data that may be used to train the classifier.

The processor then uses unsupervised machine learning to train 125 the classifier using the positive and/or negative training sets. The processor trains the classifier using adaptive learning rate optimization techniques, such as the Adam optimization algorithm, with a learning rate of $10^{-4}$. In other embodiments, the processor employs different learning rates and/or different machine learning techniques, such as linear support vector machine (linear SVM), boosting for other algorithms (e.g., AdaBoost), neural networks, logistic regression, naïve Bayes, memory-based learning, random forests, bagged trees, decision trees, boosted trees, or boosted stumps. In some embodiments, the processor uses a pre-trained classifier (e.g., VGG-19 from MATLAB), trained on a publicly available image database (e.g., ImageNet).

The trained classifier is a binary deep convolutional neural network configured to determine whether a syringe in an input image is defective, and output a label accordingly. In some embodiments, the trained classifier is a softmax deep convolutional neural network configured to take, as input, an image of a syringe, and after determining that the syringe is defective, identify types of defects within the syringe, and output a label accordingly. The output label from the classifier may be either defective or not defective, but also specifies the types of defects identified in the image of the syringe.

Prior to applying the trained classifier to an image of a syringe, the processor subtracts 130 a background from the image. To do so, the processor first detects 135 pixels corresponding to the background and a foreground of the image. A camera captures a number of sequential images (e.g., frames) of the syringe, filled with fluid, over a span of time. The camera captures the images of the syringe after the syringe has been agitated. For example, prior to the images being captured, the syringe may be centrifuged, such that the fluid spins around a center axis of the syringe. In other embodiments, the syringe is shaken. In the sequential images, objects in the fluid within the syringe settle down after being in motion. From the sequential images, the processor detects background pixels.

To detect the background pixels, the processor determines distributions of pixel intensities for a subset of the sequential images captured of the syringe (e.g., the first 10 images of a total 100 images). The processor compares the determined distributions of pixel intensities to subsequent sequential images of the syringe and based on differences in the pixel intensities, the processor determines which pixels have changed in intensity across the sequence of images. The processor determines that the pixels that have not changed across the sequence of images as background pixels, whereas those with varying intensities are foreground pixels. The background pixels remain unchanged in each of the sequential images, and indicate portions of the syringe that remain stationary after the syringe is agitated. In some embodiments, the background pixels indicate static objects, such as a scratch or particles stuck to an outside of the syringe, which are not considered contaminants. In some embodiments, the processor detects boundaries of the syringe prior to comparing the pixel intensities across the sequence of images, and assigns the pixels corresponding to the boundaries of the syringe as background pixels. In some embodiments, the processor may mistakenly determine that a background pixel is a foreground pixel, in which case the image is added to the negative training set as described in step 120 of FIG. 1.

After identifying the background pixels, the processor removes 110 the background pixels from an image of the syringe (e.g., selected from the sequence of images of the syringe) via various image processing techniques. In one embodiment, the processor uses a gaussian based segmentation algorithm to remove the background from the image, which thereby accentuates the foreground in the image. The image of the syringe with the accentuated foreground and subtracted background is herein referred to as an updated image of the syringe.

Figure 3:
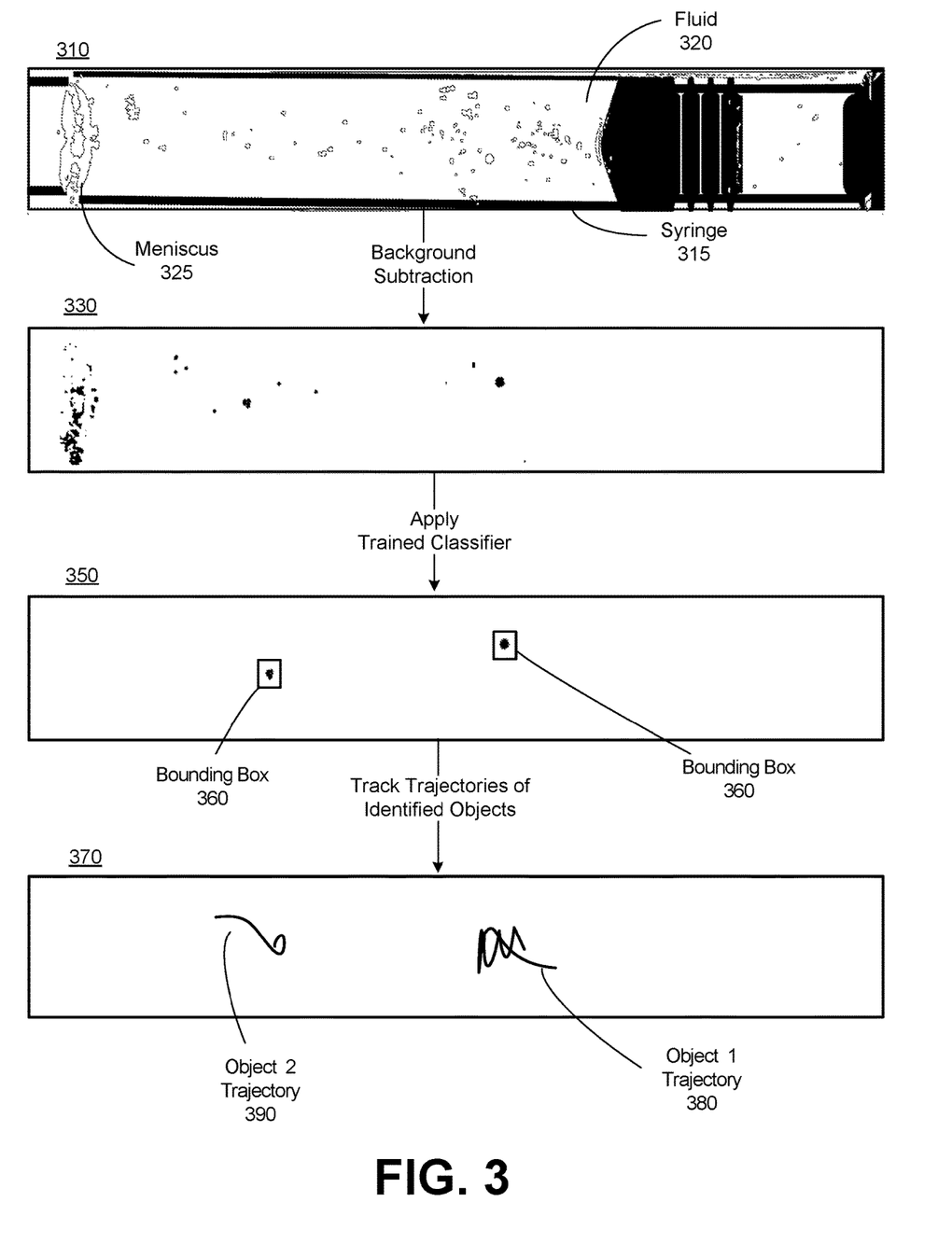
FIG. 3 shows an example process for identifying a defective syringe, in accordance with one or more embodiments.

The processor applies bounding boxes to the updated image such that each bounding box indicates a location of an object that may be a potential defect. The processor applies a bounding box to a group of foreground pixels that are within a distance of one another; a number of foreground pixels that are near each other may be indicative of an object that may be a defect. For example, a fiber floating in the fluid filled in the syringe may correspond to a group of foreground pixels all within a distance of one another. In some embodiments, a group of foreground pixels indicates an object that is not a defect, such as a bubble. In some embodiments, the processor applies multiple bounding boxes to an updated image, indicating that the syringe includes many objects that may be defects. FIG. 3 shows an example updated image with an applied bounding box.

The processor applies 115 the classifier trained to detect defects in images of syringes to the updated image. The processor provides 150 the updated image as input to the trained classifier. The trained classifier is applied to each of the bounding boxes present in the updated image. In other embodiments, the trained classifier is applied to the updated image, the updated image with the labeled bounding box, the raw image of the syringe (e.g., prior to the background being subtracted), or some combination thereof. The classifier outputs 155 a label for the input image, the label indicating whether the syringe is defective or not. In some embodiments, the classifier outputs 155 a label indicating whether an object within a bounding box is a potential defect. Responsive to determining that the object is not a defect, the classifier outputs 175 a label indicating that the syringe is not defective. Alternatively, the classifier determines that the object in the bounding box is a potential defect, and outputs a label indicating that the syringe is defective. In some embodiments, the classifier also outputs a type of defect identified within the image of the syringe. In some embodiments, responsive to the classifier outputting a label indicating that the syringe is defective and/or that an object within a bounding box is a potential defect, the processor proceeds to evaluate 160 the accuracy of the classifier by tracking a trajectory of the object within the bounding box. After tracking the trajectory of the object and determining that the trajectory is not indicative of a defect, the processor outputs 175 a label indicating that the syringe is not defective.

The processor evaluates 160 the accuracy of the classifier by tracking a trajectory of an object identified to be within the syringe. The processor identifies one or more objects within an image of a syringe found to be defective by the classifier, applies 165 heuristics to the series of images of the syringe, and determines whether the trajectory of the identified object is indicative of a defect. Using heuristics enables the processor to confirm 170 the presence of a defect after the classifier outputs a label indicating that the syringe is defective, and distinguish from false positive classification of an object as a defect. For example, after a number of foreground pixels associated with an object in the syringe are identified, isolated in a bounding box, and input into the classifier, the classifier may output a label indicating that the syringe is defective. However, the processor may identify the trajectory of the object as that of a bubble, which is not a contaminant, and therefore not a defect. The heuristics applied to a sequence of images to determine whether the trajectory is similar to that of a defect are further described with respect to FIG. 3.

FIGS. 2A-B show example training data for training a machine learning classifier that detects defects in images of syringes, in accordance with one or more embodiments. FIG. 2A shows example training data corresponding to a defective syringe. As described above, images of syringes with defects may be part of a positive training set. The processor receives a human labeled image 210 of a defective syringe. The label indicates that the syringe is defective, and may, in some embodiments, indicate a location and/or type of a potential defect 220. In some embodiments, the processor receives a human labeled background subtracted image 230, where a background of the image 210 is removed and the defect 220 is labeled. The defect 220 may be labeled as defect generically, or may more particularly be labeled as having a particular defect (e.g., dust particle).

FIG. 2B shows example training data corresponding to a non-defective syringe. Images of non-defective syringes may be a part of a negative training set. The processor receives a human labeled image 240 of a non-defective syringe. The label indicates that the syringe is not defective, and may, in some embodiments, indicate one or more bubbles 250 present in the image 240. In some embodiments, the processor receives a background subtracted image 260 of the non-defective syringe as well. In some embodiments, the background subtracted image 260 of the non-defective syringe yields an object that could be a potential defect, but is, in reality, an air bubble. A human labeling the image 240 of the non-defective syringe may label the object as a non-defect. However, in some embodiments, the human labeling the image 240 may mistake the bubble for a potential defect. Since bubbles and defects may look similar to one another, humans and/or the trained classifier may not be able to accurately distinguish between the two. Accordingly, the processor tracks a trajectory of an object that may be a potential defect, as described in further detail with respect to FIGS. 3 and 4, to confirm whether the identified object is indeed a defect.

When training the classifier, the processor extracts feature values from the labeled images of the training set. Features of the images of syringes as depicted in FIGS. 2A and 2B are associated with defective and non-defective syringes, respectively. When applied to unlabeled images of syringes, the trained classifier detects the features indicative of a non-defective or defective syringe based on the training data and accordingly outputs a label for the image of the syringe. In some embodiments, the trained classifier detects objects in an unlabeled image of the syringe, and outputs a label indicating whether the objects are potential defects.

FIG. 3 shows an example process for identifying a defective syringe, in accordance with one or more embodiments. The process is performed by a processor and is similar to that described in FIG. 1. The processor receives an image 310 of a syringe 315. The syringe 315 may be filled with a fluid 320 and includes a meniscus 325. In some embodiments, the processor receives a number of sequential images of the syringe 315 captured after the syringe 315 has been agitated, similar to image 310.

The processor generates an updated image 330 by subtracting a background of the image 310. The resultant updated image accentuates a foreground. The processor identifies the background and foreground of the image 310 by analyzing pixel intensities across a subset of the sequential images of the syringe 315. The processor determines that pixels with unchanged intensities across the subset of sequential images represent background pixels, since these pixels of unchanged intensities indicate components of the syringe 315 that remain stationary, relative to a defect, in the sequential images of the syringe 315. For example, background pixels may be associated with boundaries (e.g., walls) and/or a stopper of the syringe 315. The foreground represents pixels with intensities that varied across the sequential images, suggesting that the pixels are associated with one or more objects that moved while the syringe 315 was in motion. Accordingly, the foreground may be indicative of defects floating in the fluid 320 that may contaminate the syringe 315.

In some embodiments, the processor identifies the background of the image 310 by identifying pixels with intensities that are known to be associated with the fluid 320 in the syringe 315. Subsequently, the processor removes the identified pixels. The processor may identify and remove the background of the image 310 with image processing techniques other than those described here.

The processor then applies a bounding box 360 to a group of pixels in the foreground. The processor assigns a plurality of pixels in the foreground that are close together (e.g., less than a threshold distance away from each other) to a group. For example, when the processor identifies two pixels in the foreground that are close together, the processor assigns the two pixels to a group. The processor repeats this until there are no more neighboring pixels that would be considered to be a part of the group. The processor may use OpenCV's findContours tool, for example, to identify pixels in the foreground that are part of the same group. After designating the group of pixels, the processor applies the bounding box 360 to the group of pixels. In the case that the processor identifies several groups of pixels in the foreground, the processor applies a bounding box (e.g., similar to the bounding box 360) to each of the group of pixels. Each group of pixels is indicative of an object. In some embodiments, the processor only applies a bounding box 360 to a group of pixels that is greater than a threshold size (e.g., greater than a threshold number of pixels); any groups of pixels smaller than the threshold size may not be considered a potential defect. Each bounding box 360 is input into a trained classifier configured to identify defective syringes from images. The trained classifier outputs a label indicating that the syringe 315 is defective. In some embodiments, the trained classifier identifies and outputs a type of the defect. Note that the processor does not identify the foreground pixels near the meniscus 325 of the syringe 315 as defects. In some embodiments, the processor applies bounding boxes to foreground pixels that are a threshold distance away from the meniscus 325, since the foreground pixels near the meniscus 325 are likely to be associated with bubbles.

After the classifier outputs a label indicating that the syringe is defective and/or that an object in the syringe is a potential defect, the processor evaluates the accuracy of the classifier by confirming the presence of a defect. The processor tracks trajectories of objects within the syringe 315. Since the trajectory of a defect is visually distinct from the trajectory of a non-defect, such as a bubble, the processor can distinguish between false positive outputs of the classifier. The image 370 depicts two tracked trajectories, the trajectory 380 of object 1 and the trajectory 390 of object 2.

The processor detects trajectories of an object within the fluid 320 of the syringe 315 by tracking movement of the object over the series of images of the syringe 315 in motion. The processor receives instructions to ignore objects in motion below a stopper of the syringe and away from the meniscus 325, as bubbles, and not defects, are more likely to exist at those locations.

The processor uses heuristics to determine whether a tracked trajectory is indicative of a defect. Heuristics are rules that the processor evaluates a tracked trajectory against to determine whether a tracked trajectory is indicative of a defect. For example, a downward trajectory, such as that shown by object 1's trajectory 380, is generally indicative of a defect, since the density of the defect may cause the object to settle towards a bottom of the syringe 315. An upward trajectory, such as that shown by object 2's trajectory 390, is generally indicative of a bubble (e.g., which is not a defect). If an object stays stationary across the series of images of the syringe 315 in motion, the process may determine that the object is not a defect. For example, the object may be a scratch. In other embodiments, the trajectory of the object may suggest that the object is stuck to the outside of the syringe 315, and is therefore, not a defect. In response to detecting a trajectory that indicates that the syringe 315 is not defective, the processor modifies the label output from the classifier accordingly. In some embodiments, the processor combines trajectories of objects within the syringe 315 and evaluates the combined trajectories against the heuristics, such as when a number of objects collide and attach to one another. For example, if the combined trajectories of two objects within the syringe 315 is staggered throughout the syringe 315, the two objects are likely to be air bubbles. Thus, the processor would determine that the syringe 315 is not defective.

Figure 4:
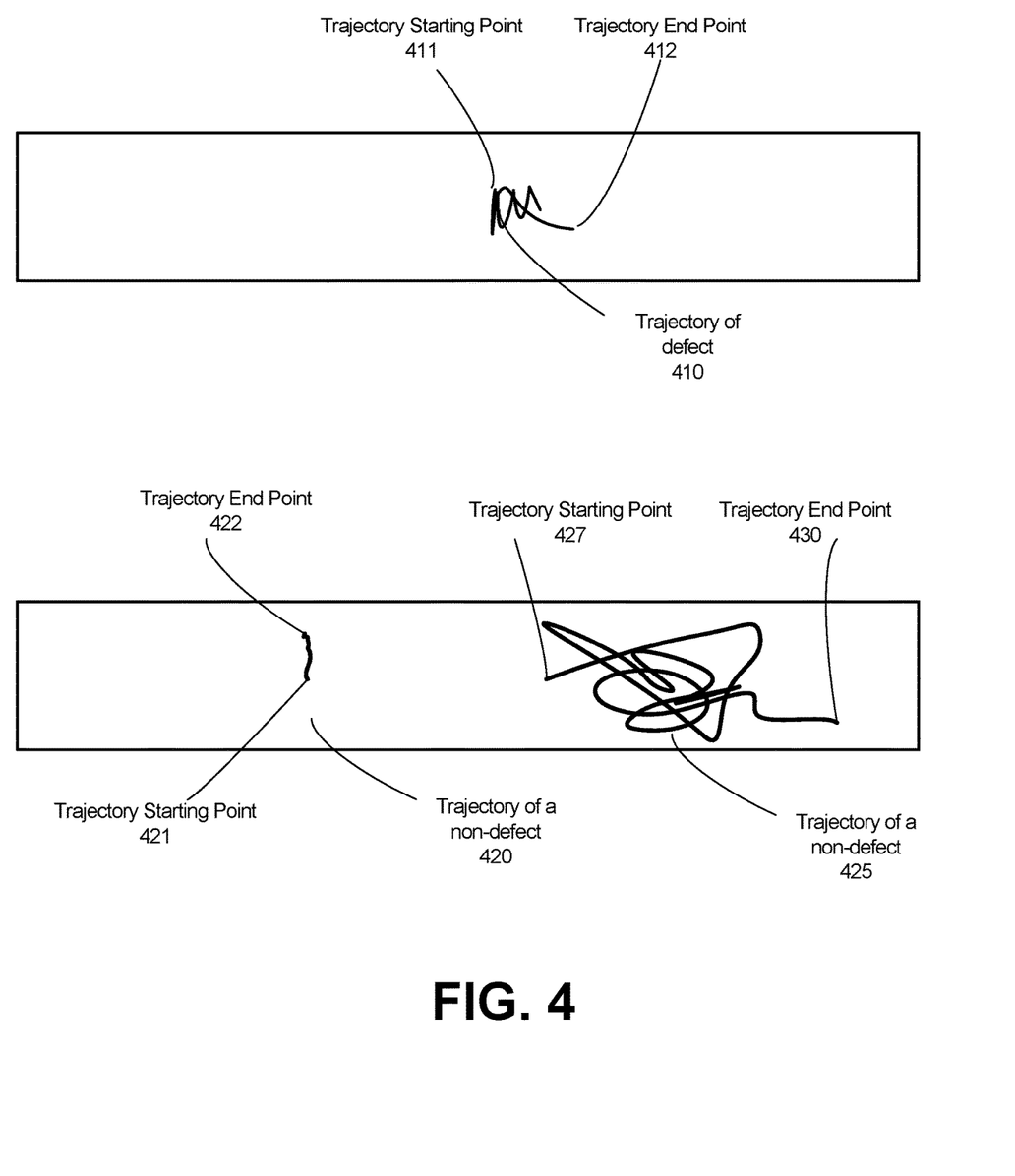
FIG. 4 shows example trajectories of objects in a defective and non-defective syringe, in accordance with one or more embodiments.

FIG. 4 shows example trajectories of objects in a defective and non-defective syringe, in accordance with one or more embodiments. As mentioned with respect to FIG. 3, the processor tracks an object's trajectory within the syringe to confirm that the object is a contaminant, or not. As per the heuristics, the processor may determine that a more complex trajectory, such as one with oscillations, and/or a trajectory generally trending downwards is indicative of a defect. In FIG. 4, the trajectory of defect 410 has several loops and slants downwards between a trajectory starting point 411 and a trajectory end point 412. Accordingly, due to the erratic trajectory, the object is most likely a defect, such as dust and/or a fiber. The processor may determine that a trajectory without many oscillations and floating upwards is indicative of a trajectory of an object that is not a defect. For example, non-defects, such as bubbles, are more likely to float upwards. The trajectory of non-defect 420 is directed upwards between a trajectory starting point 421 and a trajectory end point 422. FIG. 4 also shows another trajectory of a non-defect 425. The trajectory of the non-defect 425 may be greatly staggered across the syringe, between a trajectory starting point 427 and a trajectory end point 430, indicating that the processor has combined trajectories of two objects within the syringe. As mentioned above, a staggered trajectory is likely indicative of air bubbles, and therefore, the processor identifies the syringe as non-defective.

Additional Configuration Considerations

To save time, costs, and manual effort, a processor helps with the automated visual inspection of syringes. The processor determines whether a syringe in an image is defective. The processor applies a trained classifier to a bounding box within the image, the bounding box enclosing an object that may be a defect. The trained classifier outputs a label indicating whether the object is a potential defect. However, to mitigate false positives output by the classifier, such as when the classifier mistakenly determines that a bubble is a defect, the processor tracks a trajectory of the object over time to confirm whether the trajectory is indicative of a defect or not. Accordingly, the processor outputs a label indicating whether the syringe in the image is defective or not.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for disambiguating user data through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method for identifying whether a syringe is defective, the method comprising:
    receiving an image of the syringe, the image comprising a foreground and a background, wherein a plurality of frames of the syringe that includes the image are received, each frame being a sequential image of the syringe over a span of time;
    generating an updated image that accentuates the foreground by subtracting the background from the image;
    applying a bounding box to a group of neighboring pixels in the updated image;
    inputting the bounding box into a classifier;
    receiving, as output from the classifier, a label indicating whether the syringe is defective;
    responsive to the label indicating that the syringe is defective, tracking a trajectory of an object in the syringe across the plurality of frames; and
    evaluating an accuracy of the output from the classifier based on the trajectory.

2. The computer-implemented method of claim 1, wherein evaluating the accuracy of the output from the classifier comprises:
    determining that the trajectory of the object is a downward trajectory; and
    determining, based on the downward trajectory, that the object is a defect.

3. The computer-implemented method of claim 1, wherein evaluating the accuracy of the output from the classifier comprises:
    responsive to determining that the object is stationary across the plurality of frames, determining that the object is not a defect; and
    responsive to determining that the object is not a defect, modifying the label output from the classifier, the modified label indicating that the syringe is not defective.

4. The computer-implemented method of claim 1, wherein tracking the trajectory of the object comprises:
    tracking movement of the object within a fluid in the syringe across the plurality of frames; and
    determining the trajectory of the object from tracked movement of the object below a stopper of the syringe and greater than a threshold distance from a meniscus of fluid in the syringe.

5. The computer-implemented method of claim 4, further comprising:
    determining that the trajectory of the object is an upward trajectory;
    responsive to determining that the trajectory is an upward trajectory, determining that the object is a bubble within the fluid in the syringe; and
    modifying the label output from the classifier, the modified label indicating that the syringe is not defective.

6. The computer-implemented method of claim 1, wherein subtracting the background from the image comprises:
    identifying a static object, the static object stationary across the plurality of frames; and
    removing the static object from the image of the syringe.

7. The computer-implemented method of claim 6, wherein identifying the static object comprises:
    determining a distribution of pixel intensities across the plurality of frames; and
    identifying pixels with unchanged pixel intensities across the plurality of frames to identify the static object.

8. The computer-implemented method of claim 1, wherein the classifier is a deep convolutional neural network.

9. The computer-implemented method of claim 1, further comprising:
    inputting the image of the syringe into the classifier; and
    receiving, as output from the classifier, a label indicating whether the syringe is defective.

10. The computer-implemented method of claim 1, further comprising:
    inputting the updated image into the classifier; and
    receiving, as output from the classifier, a label indicating whether the syringe is defective.

11. The computer-implemented method of claim 1, wherein the label received as output from the classifier indicates a type of defect in the syringe.

12. The computer-implemented method of claim 11, wherein the type of defect is one of fiber and dust particles.

13. The computer-implemented method of claim 1, wherein neighboring pixels comprise pixels of a threshold intensity that are a threshold number of pixels away from each other.

14. The computer-implemented method of claim 1, further comprising:
applying a second bounding box to a second group of neighboring pixels in the updated image;
inputting the second bounding box into the classifier; and
receiving as output from the classifier, a label indicating whether the syringe is defective.

15. The computer-implemented method of claim 14, further comprising:
receiving as output from the classifier, a label indicating a type of defect associated with each of the plurality of bounding boxes.

16. A non-transitory computer readable storage medium comprising computer executable code that when executed by one or more processors causes the one or more processors to perform operations comprising:
receiving an image of the syringe, the image comprising a foreground and a background, wherein a plurality of frames of the syringe that includes the image are received, each frame being a sequential image of the syringe over a span of time;
generating an updated image that accentuates the foreground by subtracting the background from the image;
applying a bounding box to a group of neighboring pixels in the updated image;
inputting the bounding box into a classifier;
receiving, as output from the classifier, a label indicating whether the syringe is defective;
responsive to the label indicating that the syringe is defective, tracking a trajectory of an object in the syringe across the plurality of frames; and
evaluating an accuracy of the output from the classifier based on the trajectory.

17. The non-transitory computer-readable medium of claim 16, wherein evaluating the accuracy of the output from the classifier comprises:
determining that the trajectory of the object is a downward trajectory; and
determining, based on the downward trajectory, that the object is a defect.

18. The non-transitory computer-readable medium of claim 16, wherein evaluating the accuracy of the output from the classifier comprises:
responsive to determining that the object is stationary across the plurality of frames, determining that the object is not a defect; and
responsive to determining that the object is not a defect, modifying the label output from the classifier, the modified label indicating that the syringe is not defective.

19. The non-transitory computer-readable medium of claim 16, wherein tracking the trajectory of the object comprises:
tracking movement of the object within a fluid in the syringe across the plurality of frames; and
determining the trajectory of the object from tracked movement of the object below a stopper of the syringe and greater than a threshold distance from a meniscus of fluid in the syringe.

20. A system comprising:
one or more computer processors; and
a non-transitory computer readable storage medium comprising computer executable code that when executed by the one or more processors causes the one or more processors to perform operations comprising:
receiving an image of the syringe, the image comprising a foreground and a background, wherein a plurality of frames of the syringe that includes the image are received, each frame being a sequential image of the syringe over a span of time;
generating an updated image that accentuates the foreground by subtracting the background from the image;
applying a bounding box to a group of neighboring pixels in the updated image;
inputting the bounding box into a classifier;
receiving, as output from the classifier, a label indicating whether the syringe is defective;
responsive to the label indicating that the syringe is defective, tracking a trajectory of an object in the syringe across the plurality of frames; and
evaluating an accuracy of the output from the classifier based on the trajectory.

* * * * *